US011317890B2

(12) United States Patent
Sakaguchi

(10) Patent No.: US 11,317,890 B2
(45) Date of Patent: May 3, 2022

(54) CATHETER AND IMAGING APPARATUS FOR DIAGNOSIS

(71) Applicant: TERUMO KABUSHIKI KAISHA, Tokyo (JP)

(72) Inventor: Yuuki Sakaguchi, Isehara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 604 days.

(21) Appl. No.: 16/138,157

(22) Filed: Sep. 21, 2018

(65) Prior Publication Data

US 2019/0021694 A1 Jan. 24, 2019

Related U.S. Application Data

(63) Continuation of application No. PCT/JP2017/010707, filed on Mar. 16, 2017.

(30) Foreign Application Priority Data

Mar. 22, 2016 (JP) .............................. JP2016-057632

(51) Int. Cl.
*A61B 8/12* (2006.01)
*A61B 5/00* (2006.01)
(Continued)

(52) U.S. Cl.
CPC .............. *A61B 8/12* (2013.01); *A61B 5/0066* (2013.01); *A61B 5/0084* (2013.01);
(Continued)

(58) Field of Classification Search
None
See application file for complete search history.

(56) References Cited

U.S. PATENT DOCUMENTS

2014/0309536 A1* 10/2014 Douk .................... A61B 5/0084
600/478
2015/0282821 A1* 10/2015 Look ...................... A61B 17/22
606/127

(Continued)

FOREIGN PATENT DOCUMENTS

JP 2011152274 A 8/2011
WO WO 2014/188969 * 11/2014

(Continued)

OTHER PUBLICATIONS

International Search Report (PCT/ISA/210) dated May 30, 2017, by the Japan Patent Office as the International Searching Authority for International Application No. PCT/JP2017/010707.

(Continued)

*Primary Examiner* — Katherine L Fernandez
(74) *Attorney, Agent, or Firm* — Buchanan Ingersoll & Rooney PC

(57) ABSTRACT

A catheter is disclosed with a priming hole for exhaust at a distal portion of the catheter, the priming hole being used when filling with a priming solution is performed, and movably and rotatably accommodates an imaging core. The catheter includes a first connector that is provided at a rear end portion of the catheter and is supported by a fixed connector portion of a motor drive unit included in an imaging apparatus for diagnosis and a second connector that is supported by a movable connector portion of the motor drive unit. The catheter includes a reservoir, which is provided in the first connector and has a volume which decreases depending on a pull-out length of the second connector from the first connector, and a supply route, through which a priming solution injected from a priming injection port is supplied to the reservoir.

10 Claims, 11 Drawing Sheets

(51) Int. Cl.
  *A61B 8/00* (2006.01)
  *A61B 8/14* (2006.01)
  *A61B 8/08* (2006.01)

(52) U.S. Cl.
  CPC .......... *A61B 5/6852* (2013.01); *A61B 5/6876* (2013.01); *A61B 8/4461* (2013.01); *A61B 5/0073* (2013.01); *A61B 8/0891* (2013.01); *A61B 8/14* (2013.01); *A61B 8/445* (2013.01); *A61B 8/4494* (2013.01); *A61B 8/461* (2013.01); *A61B 8/5261* (2013.01)

(56) References Cited

U.S. PATENT DOCUMENTS

| | | | |
|---|---|---|---|
| 2016/0143616 A1* | 5/2016 | Okubo | A61M 39/10 600/467 |
| 2017/0071568 A1* | 3/2017 | Mitsuhashi | A61B 8/12 |
| 2017/0119260 A1* | 5/2017 | Gilbert | A61B 5/02158 |
| 2018/0214120 A1* | 8/2018 | Sakaguchi | A61M 39/1011 |

FOREIGN PATENT DOCUMENTS

| | | |
|---|---|---|
| WO | 2015/045352 A1 | 4/2015 |
| WO | 2015/045353 A1 | 4/2015 |

OTHER PUBLICATIONS

Written Opinion (PCT/ISA/237) dated May 30, 2017, by the Japan Patent Office as the International Searching Authority for International Application No. PCT/JP2017/010707.

\* cited by examiner

CATHETER AND IMAGING APPARATUS FOR DIAGNOSIS

CROSS-REFERENCES TO RELATED APPLICATIONS

This application is a continuation of International Application No. PCT/JP2017/010707 filed on Mar. 16, 2017, which claims priority to Japanese Application No. 2016-057632 filed on Mar. 22, 2016, the entire contents of both of which is incorporated herein by reference.

TECHNICAL FIELD

The present disclosure generally relates to a catheter for image diagnosis and an imaging apparatus for diagnosis using the catheter.

BACKGROUND ART

An intravascular ultrasound (IVUS) diagnostic apparatus or an optical coherence tomography (OCT) diagnostic apparatus are known as an apparatus for diagnosing a vascular lumen. A catheter that is used in such an imaging apparatus for diagnosis includes an imaging core provided with a transceiver, which emits an ultrasound wave or light and receives a reflected wave or reflected light from vascular tissue, and a catheter sheath, which accommodates the imaging core.

A liquid, as a transmission medium of a signal that is transmitted and received in the imaging core, is contained between the imaging core and the catheter sheath in some cases. For example, in a case of a diagnostic apparatus using optical coherence, a liquid is contained between the imaging core and the catheter sheath, and thereby it is possible to rather easily design an optical member that is positioned at a distal end of the imaging core, since it is possible to reduce refraction of light on an interface of the optical member and an interface of the catheter sheath by containing a liquid having a refractive index closer to a refractive index of the optical member or a refractive index of the catheter sheath than a refractive index of air. In addition, ultrasound waves are remarkably attenuated in the air. Further, when there is air between an ultrasound transducer and a subject, the ultrasound waves are almost totally reflected from interfaces between the ultrasound transducer and the subject, and thus the ultrasound waves are not transferred to the subject. In particular, in a case of the IVUS, since attenuation or total reflection of the ultrasound waves through the air is decreased as much as possible, a space between the imaging core and the catheter sheath is filled with a liquid, and a decrease in propagation efficiency of the ultrasound wave to the subject is suppressed (or reduced) in general.

In order to easily fill the space between the imaging core and the catheter sheath in the catheter with the liquid, it is desirable to rather easily discharge air (bubbles) between the imaging core and the catheter sheath in the catheter to the outside. Therefore, a priming hole for removing the air can be provided at a distal end of the catheter on a side on which the catheter is inserted into a blood vessel. Regarding a size or a use of a liquid injecting tool (for example, a syringe) for priming, it is preferable that the liquid injecting tool is attached to an end portion that is not inserted into a living body in the catheter, that is, a proximal portion of the catheter. In such a configuration, when the liquid (representatively, a saline (or saline solution); however, hereinafter, referred to as a priming solution) is injected from the proximal portion, the priming hole needs to be positioned at a catheter distal portion in order to displace air in the catheter sheath to the catheter distal portion by the liquid.

After the distal end of the catheter is positioned in the blood vessel of a diagnosis target, a so-called pull-back operation of pulling the catheter along a rotational axis of the catheter is performed while the imaging core is rotated. In order to cause the distal portion of the imaging core to retract and to increase a volume of a lumen between the imaging core and the catheter sheath by the pull-back operation, internal pressure in the distal portion of the catheter sheath is likely to become relatively negative pressure with respect to pressure outside the catheter. As a result, blood is likely to flow into the catheter sheath from the priming hole at the distal end of the catheter sheath. The blood is an opaque liquid that hinders light from transmitting through the blood. Hence, an inflow of the blood into the catheter sheath hinders a clear image from being obtained, particularly, by an OCT diagnostic apparatus.

In order to solve such a problem, a technology is disclosed in which a priming solution is forcibly fed from a side (i.e., proximal side) of the catheter on which the catheter is connected to a motor drive unit (hereinafter, MDU) included in a diagnostic apparatus, during a pull-back operation, and thereby pressure in a distal portion of the catheter is prevented from becoming negative pressure with respect to the blood (refer to International Publication No. 2015/045352).

According to International Publication No. 2015/045352, the internal pressure in a distal end of the catheter is unlikely to become the negative pressure with respect to intravascular pressure during the pull-back operation, thus it is possible to suppress inflow of the blood into a catheter sheath, and thus it is possible to reconstruct an image having a higher image quality.

However, according to International Publication No. 2015/045352, whenever a diagnosis is made, it is necessary to perform a priming operation on the catheter, an operation of filling a cylinder separate from the catheter with a priming solution, and further an operation related to connection between the catheter and the cylinder on which the priming operation and the operation of filling are finished.

SUMMARY OF THE INVENTION

A catheter is disclosed having improved operability in which it is possible to fill a priming solution supply source by which a decrease in internal pressure of the catheter during pull-back is suppressed by a relatively simpler operation.

In accordance with an exemplary embodiment, a catheter for an image diagnosis is disclosed that is provided with a priming hole for exhaust at a distal portion, the priming hole being used when filling with a priming solution is performed, and that movably and rotatably accommodates an imaging core, the catheter including: a first connector that is supported by a fixed connector portion of a motor drive unit included in an imaging apparatus for diagnosis and a second connector that is supported by a movable connector portion of the motor drive unit, the first and second connectors being provided at a proximal portion; a reservoir that is provided in the first connector and has a volume which decreases depending on a pull-out length of the second connector from the first connector; and a supply route through which a part of a priming solution injected from a priming injection port provided in advance is supplied to the reservoir. The supply route is spatially connected to the priming hole.

In accordance with another embodiment, a catheter is disclosed for an image diagnosis, the catheter comprising: a first connector configured to be supported by a fixed connector portion of a motor drive unit included in an imaging apparatus for diagnosis; a second connector configured to be supported by a movable connector portion of the motor drive unit, the first and second connectors being located at a proximal portion of the catheter; a reservoir in the first connector, the reservoir having a volume which decreases depending on a pull-out length of the second connector from the first connector; and a supply route configured to supply a priming solution injected from a priming injection port to the reservoir, and wherein the supply route is connected to a priming hole on a distal portion of the catheter.

In accordance with a further embodiment, a catheter is disclosed for an image diagnosis, the catheter comprising: a first connector configured to be supported by a fixed connector portion of a motor drive unit included in an imaging apparatus for diagnosis; a second connector configured to be supported by a movable connector portion of the motor drive unit, the first and second connectors being located at a proximal portion of the catheter; a first reservoir in the first connector, the first reservoir having a volume which decreases depending on a pull-out length of the second connector from the first connector; a guide-through route through which the first reservoir and the catheter sheath are connected to each other, the guide-through route having a first valve interposed between the first reservoir and the catheter sheath, the first valve configured to allow a priming solution to flow only in one direction into a catheter sheath provided with a priming hole at a distal end of the catheter sheath; and a second reservoir that is connected to the first connector with a second valve interposed between the first connector and the second valve, the second valve configured to allow the priming solution to flow only in one direction to the first reservoir.

In accordance with another embodiment, a method is disclosed of imaging a body lumen inside of a living body, the method comprising: inserting a catheter into the living body, the catheter including a first connector configured to be supported by a fixed connector portion of a motor drive unit included in an imaging apparatus for diagnosis, a second connector configured to be supported by a movable connector portion of the motor drive unit, the first and second connectors being located at a proximal portion of the catheter, a reservoir in the first connector, the reservoir having a volume which decreases depending on a pull-out length of the second connector from the first connector, and a supply route configured to supply a priming solution injected from a priming injection port to the reservoir, and wherein the supply route is connected to a priming hole on a distal portion of the catheter; priming the catheter and the reservoir with the priming solution; generating a vascular cross-sectional image from a signal obtained by an imaging core of the catheter; and executing a pull-back operation of the catheter along a rotational axis of the catheter which the imaging core is rotating and supplying the priming solution of the reservoir to the distal portion of the catheter via the supply route.

According to the present disclosure, a priming solution supply source can be filled by which a decrease in internal pressure of the catheter during pull-back is suppressed only by a priming operation on the catheter which is usually performed, and thus operability can be improved. In addition, from a point of view of a user, there is no increase in special equipment.

BRIEF DESCRIPTION OF THE DRAWINGS

The accompanying figures are included in the specification, constitute a part of the specification, represent embodiments of the present disclosure, and are used for the description of principles of the present disclosure together with the description of the embodiments.

DESCRIPTION OF EMBODIMENTS

Hereinafter, embodiments of the present invention will be described in detail with reference to the accompanying figures. Note that the embodiments to be described below are preferred specific examples of the present disclosure, and thus various technically preferable limitations are provided; however, the scope of the present disclosure is not limited to aspects of the examples unless there is no particular statement indicating a limitation to the present disclosure in the following description.

First Embodiment

Note that an imaging apparatus for diagnosis in an embodiment is described as an apparatus having both of an IVUS function and an OCT function. Since the present disclosure is also applicable to an apparatus having one function of the two functions or an imaging apparatus for diagnosis using an optical sensor by a near infrared spectroscopy (NIRS) other than optical coherence tomography, the present disclosure is not limited to such respect.

Figure 1:
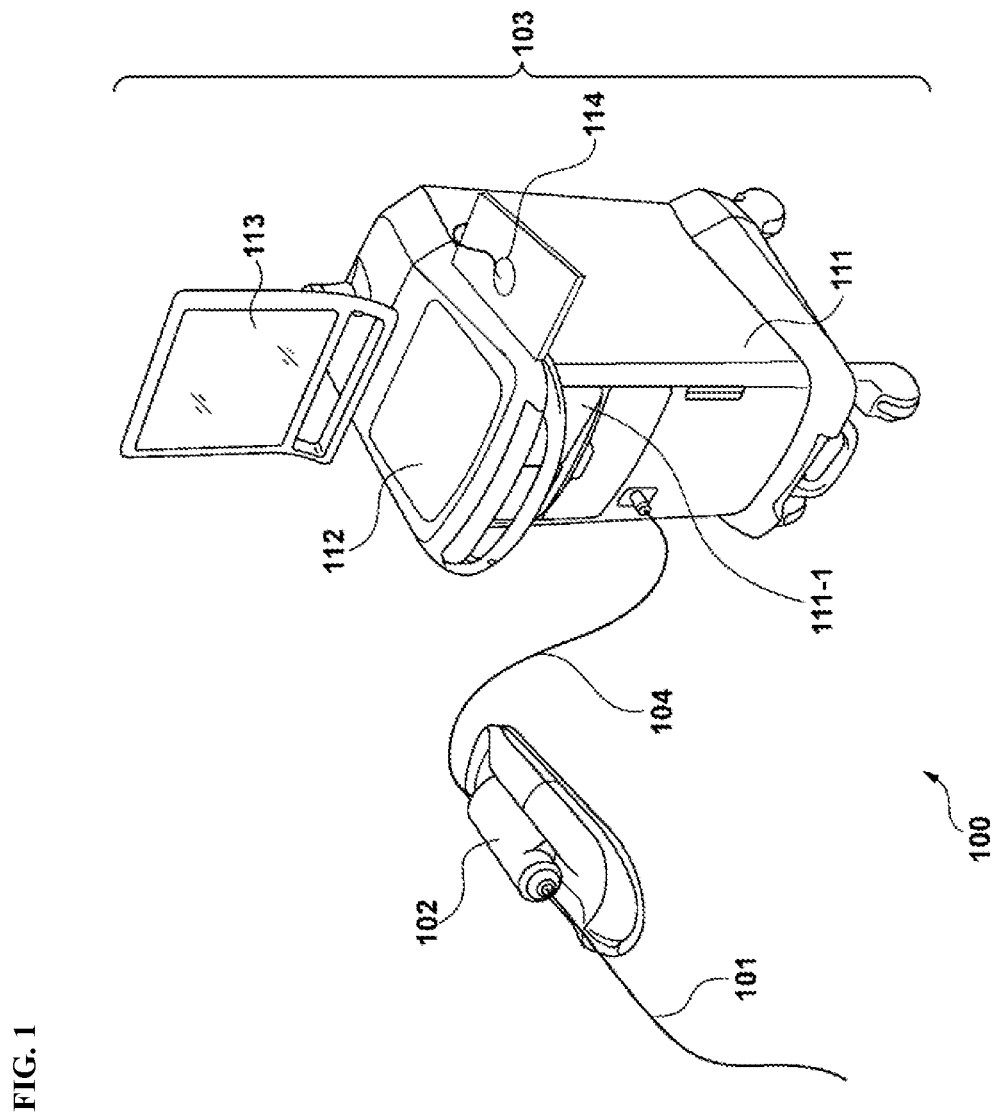
FIG. 1 is a view showing an external configuration of an imaging apparatus for diagnosis according to an embodiment.

FIG. 1 is a view showing an example of an external configuration of an imaging apparatus 100 for diagnosis according to an embodiment of the present disclosure.

As shown in FIG. 1, the imaging apparatus 100 for diagnosis includes a catheter 101, a motor drive unit (hereinafter, MDU) 102, and an operation control apparatus 103, and the MDU 102 and the operation control apparatus 103 are connected to each other via a cable 104 accommodating a signal wire or an optical fiber.

In the operation control apparatus 103, 111 represents a main body control unit. The main body control unit 111 generates line data from a rotational center position in a radial direction in response to a signal (ultrasound waves emitted toward vascular tissue and reflected waves of light) obtained by an imaging core accommodated in the catheter 101. In this manner, a vascular cross-sectional image is generated based on the ultrasound waves through interpolation processing of the line data.

In accordance with an aspect, 111-1 represents a printer and a DVD recorder and prints a process result in the main body control unit 111 or stores the process result as data. Note that a storage unit of the process result may be a server, a USB, a memory, or the like and may be any type of unit.

In accordance with another aspect, 112 represents an operation panel, and a user inputs various setting values and instructions via the operation panel 112.

In accordance with a further aspect, 113 represents a monitor (for example, an LCD) as a display apparatus, and various cross-sectional images generated in the main body control unit 111 are displayed on the monitor 113.

In accordance with an aspect, 114 represents a mouse as a pointing device (coordinate input device).

The catheter 101 is directly inserted into a blood vessel. The catheter 101 has a structure of accommodating the imaging core that is rotatable and movable in a longitudinal direction of the catheter. A distal end of the imaging core is provided with a housing that houses an ultrasound transceiver, which generates an ultrasound wave based on a signal that has been transferred from the imaging apparatus 100 for diagnosis, receives a reflected ultrasound wave from the vascular tissue, and converts the reflected ultrasound wave into an electric signal, and an optical transceiver, which continuously transmits transferred light (measurement light) into the blood vessel and continuously receives the reflected light from the inside of the blood vessel. A drive shaft for transmitting a rotational and moving force from the MDU 102 to the imaging core is connected to the housing. In other words, the imaging core is configured to have the housing and the drive shaft. The imaging apparatus 100 for diagnosis measures a state of the inside of the blood vessel by using the catheter 101 that accommodates the imaging core.

In accordance with an exemplary embodiment, the MDU 102 functions as a relay unit between the ultrasound transceiver and the optical transceiver and the operation control apparatus 103 in the imaging core in the catheter 101 in a state in which a part of the MDU which engages with a connection section of a rear end of the catheter 101 is held and the MDU is connected to the catheter 101. In addition, the MDU 102 drives a built-in motor, thereby performing a process of pulling a proximal-side inner tube (or hand-side inner tube) and the drive shaft with respect to a proximal-side outer tube (or hand-side outer tube) of the catheter 101 and controlling rotation of the drive shaft.

In addition, the MDU 102 includes various switches and buttons, and thus a user (doctor or the like) can operate the switches and buttons, thereby performing rotation drive of the imaging core in the catheter 101 and pull-back (moving of the imaging core).

An actual pull-back scanning process of a blood vessel of a patient is known; however, the process is briefly described here.

While the user sees an X-ray image, the user checks that a distal portion of the catheter 101 moves to a position of a diagnosis target. Then, the user operates the MDU 102 and instructs the pull-back. As a result, while the housing that is positioned at the distal end of the catheter 101 and houses the ultrasound transceiver and the optical transceiver rotates, the housing moves along the inside of the blood vessel.

For example, the ultrasound transceiver emits and receives ultrasound waves 512 times for one rotation and transmits a received signal toward the operation control apparatus 103 via the MDU 102. The operation control apparatus 103 receives the signal and performs predetermined arithmetic processing, thereby obtaining line data of 512 lines extending from the rotation center of the transceiver in a radiation direction. The line data is rather dense at the center position of the rotation and is relatively sparse (i.e., thinly distributed) from each other farther apart from the rotation center. Hence, in order to obtain a two-dimensional image viewed by a human, the operation control apparatus 103 performs interpolation processing between lines and performs a process of generating pixels between lines. As a result, a vascular tomographic image (ultrasound cross-sectional image) can be generated in a direction orthogonal to an axial direction of the blood vessel.

For example, similar to the ultrasound transceiver, the optical transceiver also emits light 512 times for one rotation, receives reflected light from the vascular tissue, and transmits received light (measurement light) toward the operation control apparatus 103 via the MDU 102. Therefore, an optical fiber is accommodated in the drive shaft in the imaging core, and the optical transceiver and the operation control apparatus 103 are optically connected via the MDU 102. The operation control apparatus 103 synthesizes the measurement light from the optical transceiver and reference light through a known length by a photocoupler and generates interference light. The interference light is converted into digital data via a photodetector and an ND converter. Fast Fourier transform processing is performed on the obtained digital data, and the line data is obtained. The subsequent processes are substantially similar to those of the ultrasound transceiver. The interpolation processing is performed, and a vascular tomographic image (optical coherence cross-sectional image) of a plane orthogonal to the axis of the blood vessel is generated.

The vascular tomographic images at positions on the axis of the blood vessel, which are obtained whenever the ultrasound transceiver turns one rotation, are joined, and thereby a three-dimensional image of the blood vessel can be generated by using the ultrasound waves. In addition, the vascular tomographic images at positions on the axis of the blood vessel, which are obtained whenever the optical transceiver turns one rotation, are joined, and thereby a three-dimensional image of the blood vessel can be generated by using the optical coherence. A doctor diagnoses a blood vessel of a patient from an image obtained by such scanning.

Figure 2:
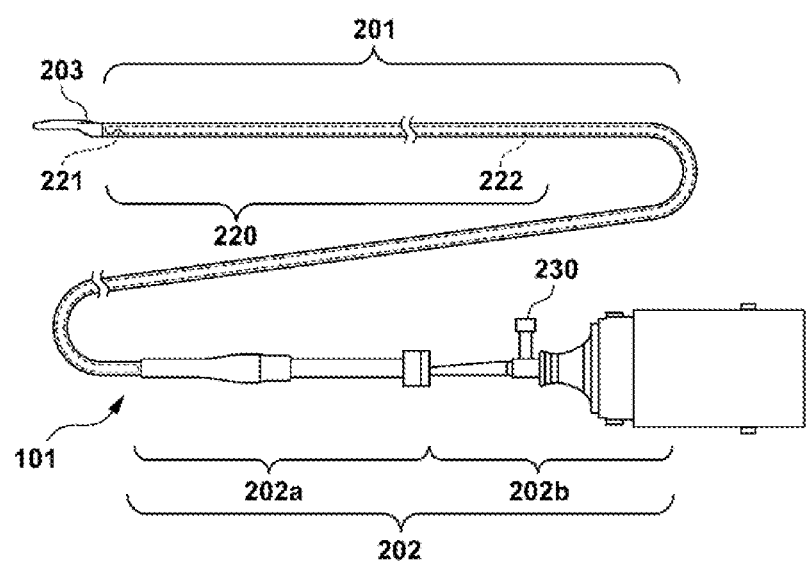
FIG. 2 is a view showing a structure of a catheter in the embodiment.

As described above, a motion overview during the pull-back scanning in the embodiment is provided. Next, the catheter 101 in the embodiment will be described with reference to FIG. 2.

The catheter sheath 201 houses, inside the lumen of the catheter sheath 201, a housing 221, in which the ultrasound transceiver that transmits and receives the ultrasound wave and the optical transceiver that transmits and receives light are disposed, and an imaging core 220, which includes an electric signal cable and an optical fiber cable inside and is configured to have a drive shaft 222 that transmits a rotational drive force for rotating the housing, along almost the entire length of the catheter sheath 201.

The proximal-side portion (or hand-side portion) 202 includes a first connector 202a, which is integrally configured to a proximal end of the catheter sheath 201, and a second connector 202b, which is configured to rotatably fix the drive shaft 222. In addition, the second connector 202b is provided with an injection port (hereinafter, a priming port) 230 through which a priming solution is injected so as to fill the inside of the catheter 101 with a saline (or saline solution) the like (hereinafter, a priming solution). In a case where the priming solution is injected from the priming port 230, the priming solution is injected between a proximal-side inner tube (or hand-side inner tube) to be described below (reference sign 271 in FIG. 3 to be described below), which is accommodated in the second connector 202b, and a support tube (a reference sign 272 in FIG. 3) for accommodating and supporting the imaging core 220, and the priming solution flows to the side of the first connector 202a. Note that the second connector 202b is provided with a sealing member (not shown) for sealing the priming solution, and thus the priming solution does not leak from the second connector 202b.

In a state in which the first connector 202a is fixed, the MDU 102 performs an operation of pulling the second connector 202b, thereby performing movement of the imaging core 220 in the catheter 101 in an axial direction of the imaging core 220. In addition, the MDU 102 rotates the imaging core 220 via a movable connection section that connects a second connector. As a result, the pull-back of the movement in the axial direction and the rotation of the ultrasound transceiver and the optical transceiver mounted in the housing 221 that is positioned at the distal end of the imaging core 220 is performed.

Next, a structure of the first connector 202a in the embodiment will be described with reference to FIG. 3.

The first connector 202a is divided into a proximal-side (or hand-side) outer tube 250, a unit connector 251, a catheter shaft relay connector 252, and a guide-through route 253. The unit connector 251 is provided with a latch section (for example, a concave portion) 251a for being fixed to the MDU 102. In addition, the catheter shaft relay connector 252 is provided with an air hole 252a. Further, the distal end of the catheter sheath 201 is also provided with a priming hole 206 for causing air in the catheter to let out during a priming operation.

Figure 3:
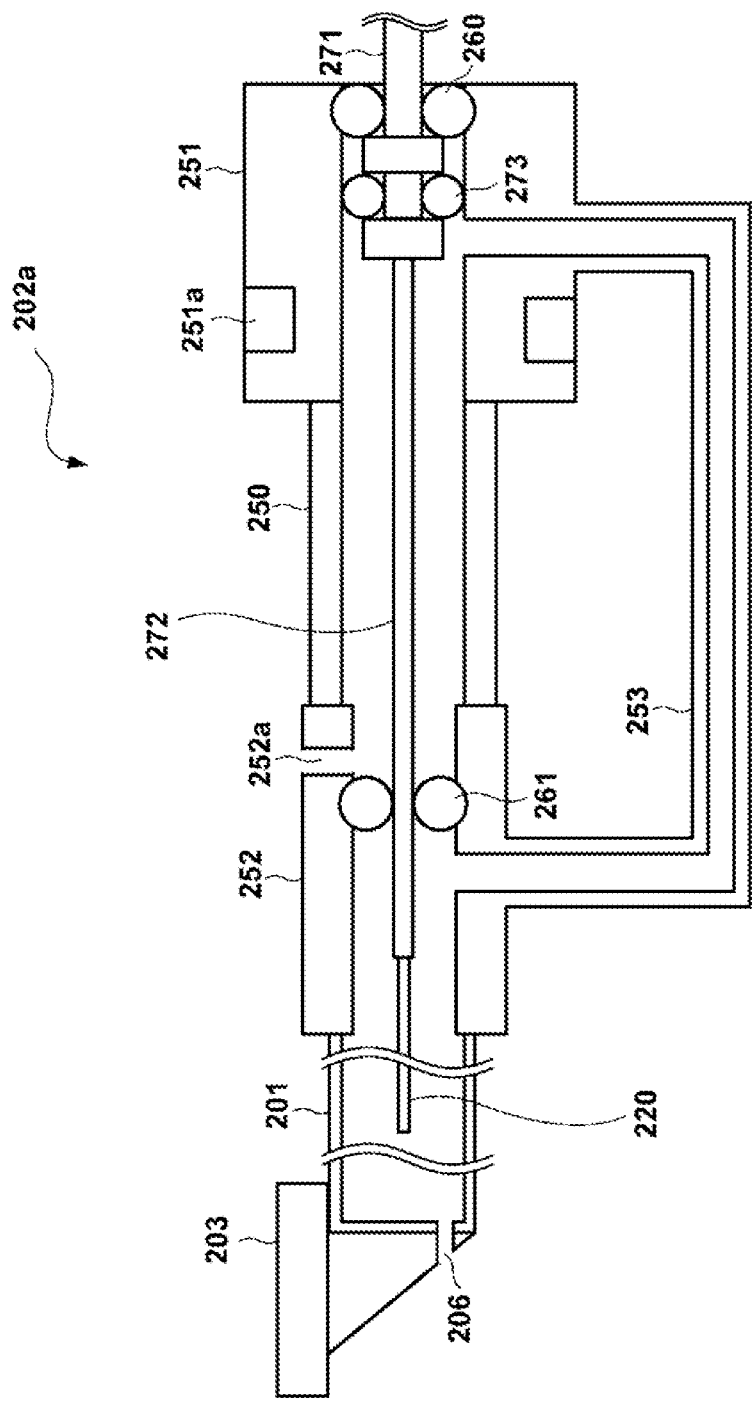
FIG. 3 is a cross-sectional view showing a structure of a first connector of a catheter in accordance with a first embodiment.

The first connector 202a movably houses a support tube 272 that accommodates and supports the imaging core 220 extending from the second connector 202b and a proximal-side inner tube (or hand-side inner tube) 271 that accommodates the support tube 272 as shown in FIG. 3. The first connector 202a has a sealing member 260 for maintaining a sealing state with the proximal-side inner tube 271 and a sealing member 261 for maintaining a sealing state with the support tube 272. The sealing members 260 and 261 are configured of an O-ring, for example, and positions of the sealing members are fixed to positions shown in FIG. 3.

On the other hand, a sealing member 273 is provided also at a distal portion of the proximal-side inner tube 271. The proximal-side inner tube 271 is movable in the first connector 202a as described above. Accordingly, the sealing members 260 and 261, the proximal-side inner tube 271, the support tube 272, and the sealing member 273 together function just like a cylinder.

In addition, as shown in FIG. 3, in a state (pull-back state) in which the proximal-side inner tube 271 (the second connector 202b) is pulled to the right end to the maximum extent, a connection state is obtained between a space in the guide-through route 253 and the air hole 252a. In a case where the proximal-side inner tube 271 is pushed by a predetermined length or more from the state in FIG. 3, the space in the guide-through route 253 and the air hole 252a are blocked from each other, and a connection state is obtained between the space in the guide-through route 253 and a space defined between the sealing member 260 and the sealing member 273.

Note that, as will be clearly described below, a movable range of the proximal-side inner tube 271 in the first connector 202a is larger than a movement range of the proximal-side inner tube 271, which is obtained by the MDU 102 during the pull-back operation during an operation.

As described above, the structure of the first connector 202a in the embodiment is described. Next, a motion of the catheter 101 in the embodiment will be described with reference to FIGS. 4A to 4C.

As shown in FIG. 3, in a state in which the proximal-side inner tube 271 is pulled to the maximum extent to the right side in FIG. 3, the user injects the priming solution from the priming port 230 (refer to FIG. 2) provided in the second connector 202b. In this case, the priming solution flows into the first connector 202a from the second connector 202b through a space between the support tube 272 and the imaging core 220.

Figure 4A:
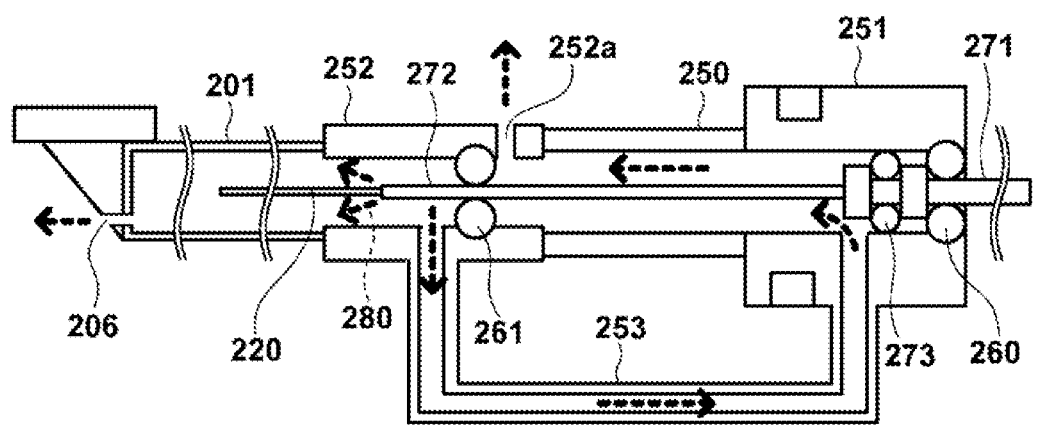
FIGS. 4A, 4B, and 4C are views illustrating a motion of the catheter in accordance with the first embodiment.

FIG. 4A shows a state of the motion of the catheter in accordance with an embodiment. The priming solution is released from a distal end of the support tube 272 as shown by a dashed arrow 280. Hence, when the user continues the injection operation of the priming solution, the priming solution passes through the inside of the catheter sheath 201 and is finally discharged from the priming hole 206 at the distal end of the catheter sheath 201. In addition, the priming solution passes through the guide-through route 253, flows into the space between the sealing member 261 and the sealing member 273, and is finally discharged from the air hole 252a. The discharge of the priming solution from the priming hole 206 and the air hole 252a represents a signal indicating that the inside of the catheter 101 is filled with the priming solution.

Next, the user performs an operation of pushing the second connector 202b into the first connector 202a. When the pushing operation is performed, the proximal-side (or hand-side) inner tube 271 moves in a direction shown by a solid arrow 281 in FIG. 4B. The movement of the proximal-side inner tube 271 is performed in a direction in which a volume between the sealing member 260 and the sealing member 273 increases. In other words, pressure in the space between the sealing member 260 and the sealing member 273 becomes negative pressure. Accordingly, the priming solution in the catheter 101 flows into the space between the sealing member 260 and the sealing member 273 as shown by a dashed arrow 282 in the figure along the guide-through route 253. As described above, the space interposed between the sealing member 260 and the sealing member 273 functions as a reservoir of the priming solution.

Figure 4B:
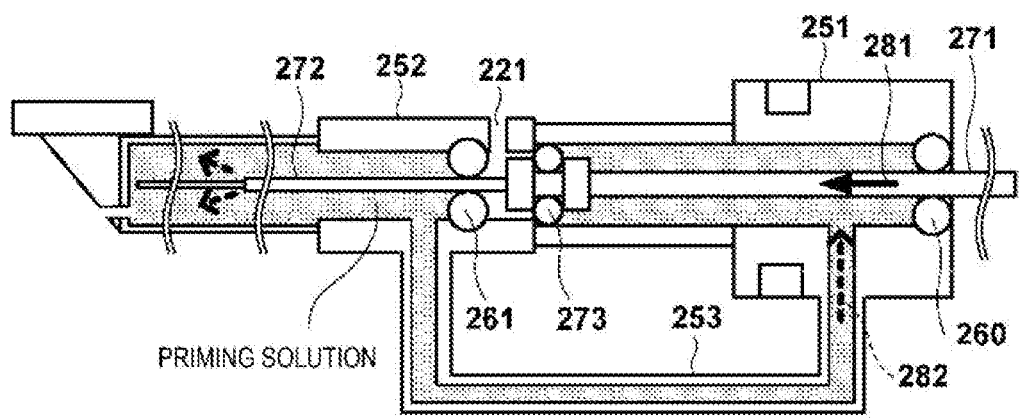

When the pushing of the proximal-side inner tube 271 is completed, the inside of the catheter sheath 201, the inside of the guide-through route 253, and the space between the sealing member 260 and the sealing member 273 are filled with the priming solution, as shown in FIG. 4B, and preparation of the operation is completed.

Figure 4C:
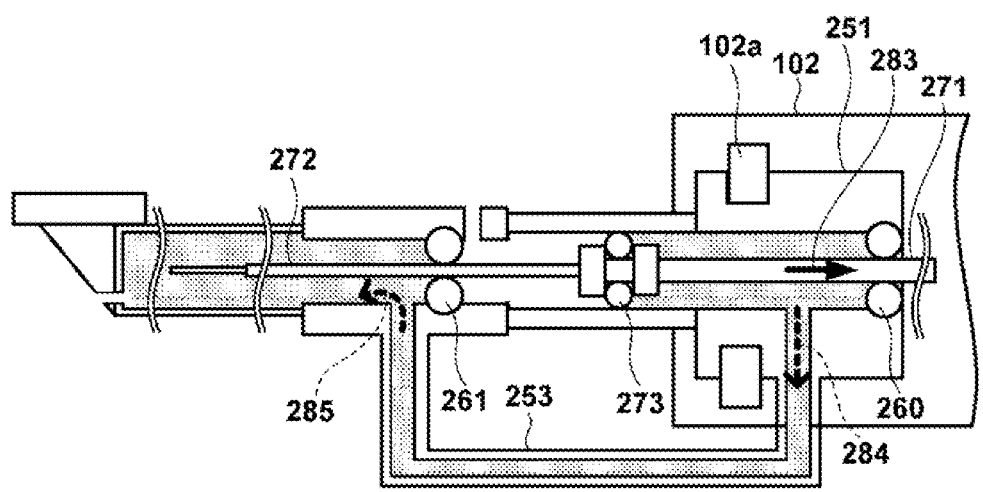

Next, a motion during the pull-back operation will be described. FIG. 4C shows a state in which the catheter 101 is installed in the MDU 102. In FIG. 4C, reference sign 102a represents a support member that is provided in the MDU 102 and fixedly supports a latch section 251a of the unit connector 251 of the first connector 202a. In addition, the second connector 202b is connected to a movable connector (not shown) of the MDU 102. The movable connector controls rotation of the imaging core 220 accommodated in the second connector 202b in order to pull out (pull-back) the second connector 202b from the first connector 202a. Note that the present disclosure does not focus on a structure of the MDU 102, and thus the description of the structure of the MDU 102 is not further provided in detail than the above description.

When the user operates the MDU 102 and inputs an instruction of the pull-back, the MDU 102 starts to move the movable connector and rotates the imaging core 220 in the second connector 202*b*. As a result, the proximal-side inner tube 271 moves to the right side (i.e., the side operated by the operator) as shown by a solid arrow 283 in FIG. 4C, and the imaging core 220 in the catheter sheath 201 also moves toward the right side in FIG. 4C. When the proximal-side inner tube 271 moves along the solid arrow 283, the volume of the space defined between the sealing member 260 and the sealing member 273 decreases, and thus the pressure of the space between the sealing member 260 and the sealing member 273 increases. Hence, the priming solution present in the space is pushed to the guide-through route 253 as shown by a dashed arrow 284 in FIG. 4C and is supplied to the catheter sheath 201 as shown by a dashed arrow 285. As a result, a decrease in the internal pressure of the catheter sheath 201 is suppressed. Hence, it is also possible to suppress flow of blood into the catheter from the priming hole 206 provided at the distal portion of the catheter sheath 201.

Note that a pushing amount of the priming solution per unit time due to the movement of the sealing member 273 during the pull-back is equal to or greater than an amount of decrease in volume of the imaging core 220 present in the catheter sheath 201 per unit time. However, when a forward operation of pushing the proximal-side inner tube is considered, the pushing amount of the priming solution per unit time due to the movement of the sealing member 273 during the pull-back is desirably equal to an amount of decrease in volume of the imaging core 220 present in the catheter sheath 201 per unit time. Here, since the pushing amount per unit time is determined by a product of "a cross-sectional area of a space between the proximal-side outer tube 250 and the proximal-side inner tube 271" and "a movement length of the proximal-side inner tube per unit time", those values may be appropriately set, and manufacturing may be performed.

According to the structure of the catheter 101 of the first embodiment described above, it is possible to fill a priming solution supply source (reservoir) by which a decrease in catheter internal pressure during pull-back is suppressed only by the priming operation on the catheter which is usually performed, and thus it is possible to improve operability. In addition, from a point of view of a user, there is no increase in special equipment.

Note that, in the description of the embodiment, both of the ultrasound transceiver and the optical transceiver are mounted in the imaging core 220 of the catheter 101; however, the embodiment may be applied to a catheter in which only one transceiver is mounted, and thus the present disclosure is not limited to the embodiment described above.

In addition, in the description of the first embodiment, both of the guide-through route 253 and the proximal-side outer tube 250 are provided to be spatially separated from each other; however, the inside of the proximal-side outer tube 250 may have a large thickness, and thus the guide-through route 253 may be secured in the proximal-side outer tube 250.

Second Embodiment

Figure 5:
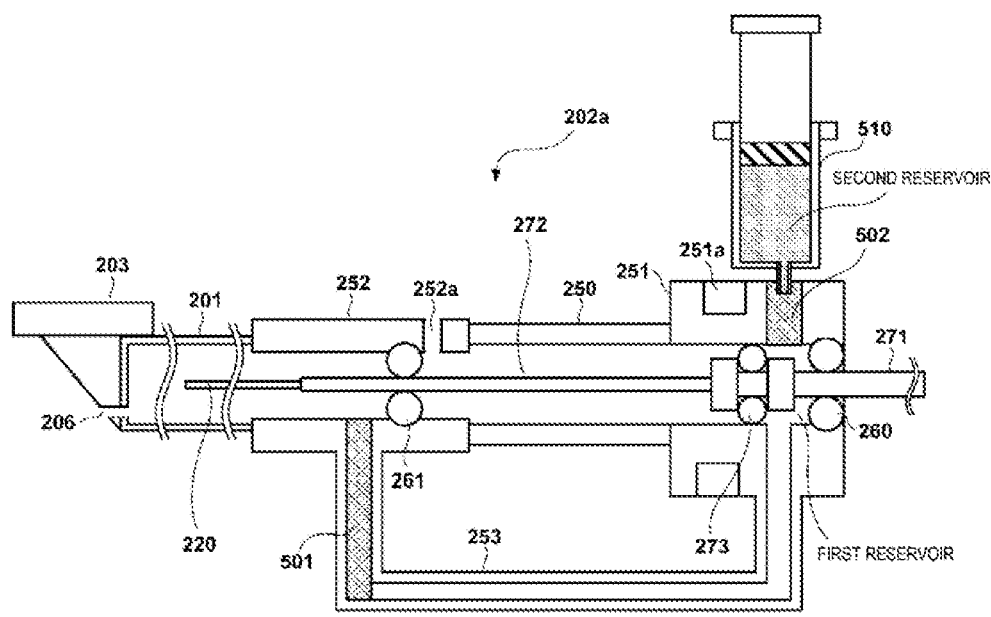
FIG. 5 is a cross-sectional view showing a structure of a first connector of a catheter in accordance with a second embodiment.

Next, a second embodiment according to the present disclosure will be described. FIG. 5 shows a structure of the first connector 202*a* in the second embodiment. The same reference signs are assigned to the same configurations as those in FIG. 3 in the first embodiment, and the description of the reference signs is omitted.

Note that, also in the second embodiment, the space interposed between the sealing member 260 and the sealing member 273 functions as the reservoir of the priming solution. In the second embodiment, a syringe 510 that functions as another reservoir is used. In order to distinguish between both of the reservoirs, as shown in FIG. 5, a space interposed between the sealing member 260 and the sealing member 273, in which the priming solution is stored, is referred to as a first reservoir, and a space in the syringe 510 which contains the priming solution is referred to as a second reservoir. In the embodiment, the second reservoir is described by using the syringe; however, any type of supply section may be used without particular limitation as long as the supply section has the same function.

The catheter 101 of the second embodiment has the two following features.

(1) A first valve 501 that allows a fluid to pass only in one direction from the guide-through route 253 to the catheter sheath 201 is provided in the guide-through route 253.

(2) A connector that connects the syringe 510 to the unit connector 251 is provided, and a second valve 502 that allows a fluid to pass only in one direction from the second reservoir to the first reservoir is provided in the connector.

Here, the valves 501 and 502 can be duckbill valves, for example; however, any type of valve may be used without particular limitation as long as the valve has the same function.

Note that, in the case of the second embodiment, since it is possible to achieve a non-connection state between the space in the guide-through route 253 and the air hole 252*a*, a movable range of the proximal-side inner tube 271 can be relatively shortened compared to the movable range of the proximal-side inner tube 271 in the first embodiment. In addition, a pushing amount of the priming solution from the first reservoir during the pull-back operation is larger than an amount of decrease in volume of the imaging core in the catheter sheath 201.

Hereinafter, the motion of the catheter 101 in the second embodiment in the configuration described above is described in order by using FIGS. 6A to 7B.

Figure 6A:
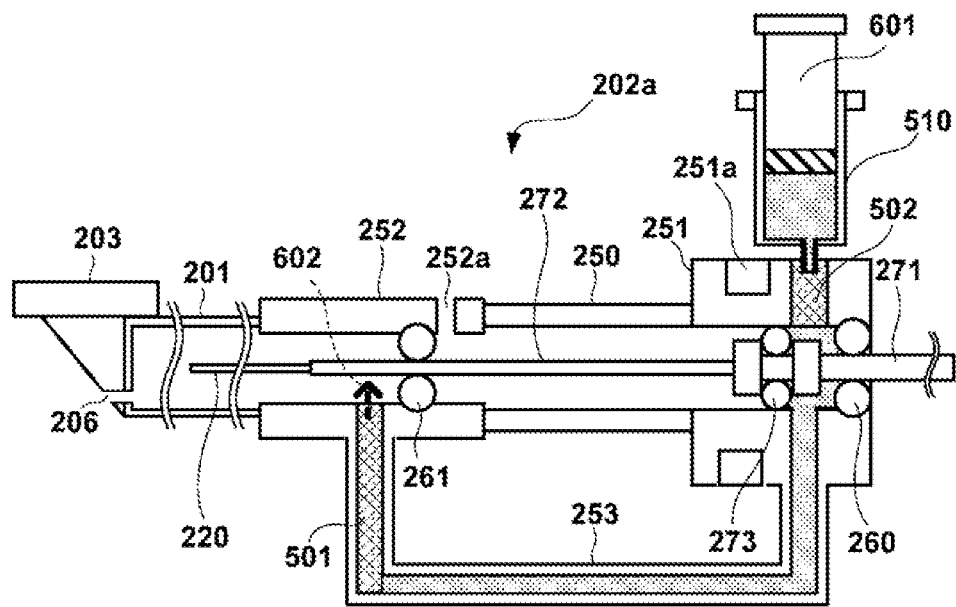
FIGS. 6A and 6B are views for illustrating a motion of the catheter in accordance with the second embodiment.

During Priming: FIG. 6A

As shown in the figure, in a state (pull-back state) in which the proximal-side inner tube 271 is pulled to the maximum extent to the right side, the user performs an operation of pushing the syringe 510 in a direction of a solid arrow 601 in FIG. 6A. Since the valve 502 is a one-way valve as described above, the priming solution flows from the second reservoir through the first reservoir to the guide-through route 253. As a result, the air in the first reservoir and inside the guide-through route 253 is pushed into the catheter sheath 201 via the valve 501. The priming solution flows from the valve 501 to the catheter sheath 201 as shown by a dashed arrow 602 in FIG. 6A, and the first reservoir and the inside of the guide-through route 253 are filled with the priming solution.

Figure 6B:
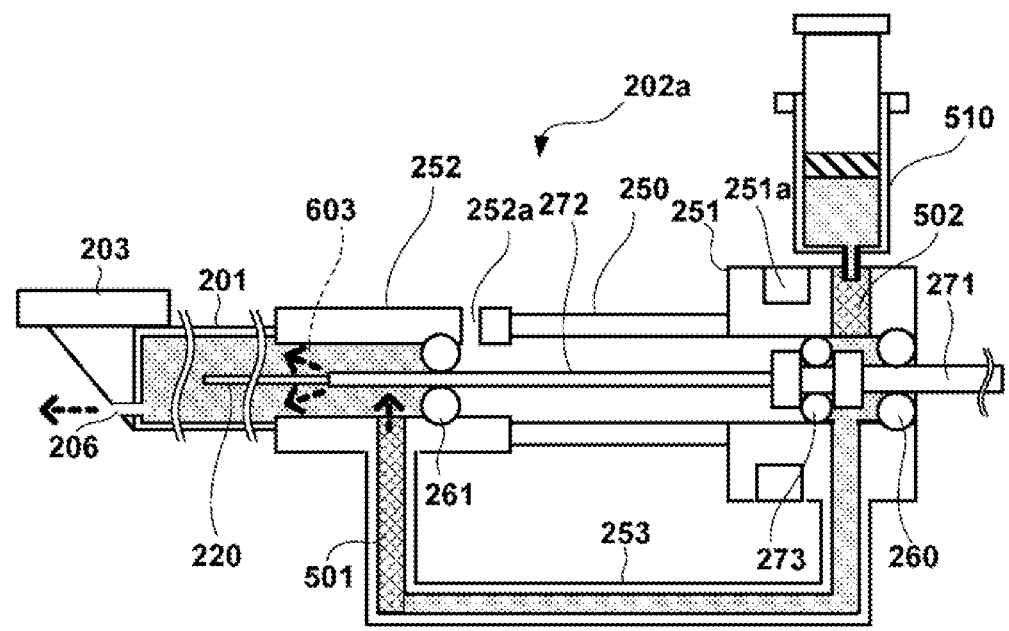

During Priming: FIG. 6B

Similar to the first embodiment, the user performs an operation of injecting the priming solution from the priming port 230 of the second connector 202*b* of the catheter 101. As a result, as shown by a dashed arrow 603 in FIG. 6B, the priming solution flows from the space between the support tube 272 and the imaging core 220 into the catheter sheath 201. Note that the priming solution that flows from the second connector 202b into the catheter sheath 201 by the valve 501 does not flow to the guide-through route 253. In addition, the user checks that the priming solution is released from the priming hole 206.

Figure 7A:
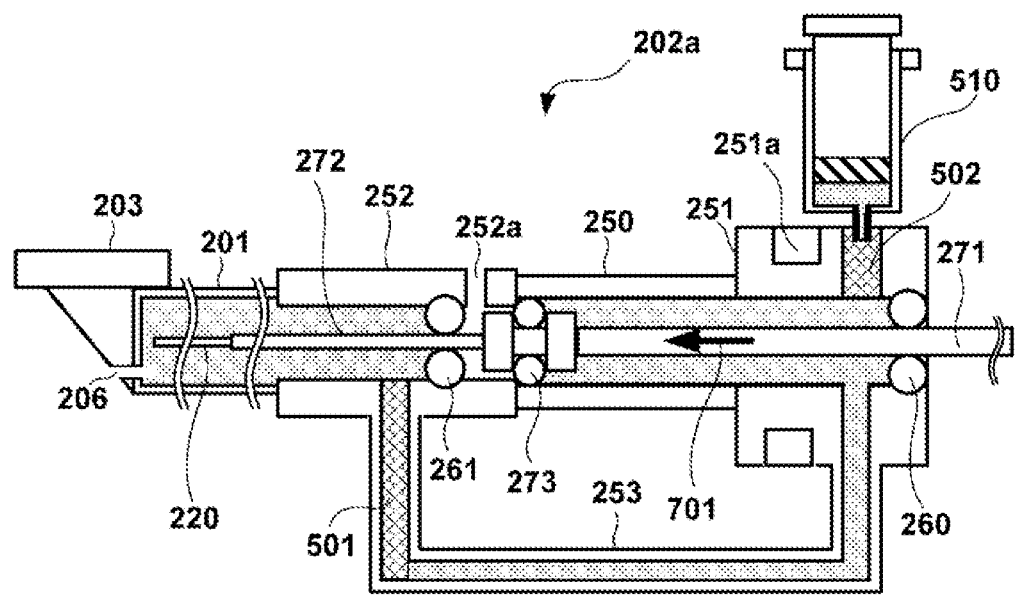
FIGS. 7A and 7B are views for illustrating another motion of the catheter in accordance with the second embodiment.

During Forward: FIG. 7A

The user performs an operation of pushing the proximal-side inner tube 271 in a direction shown by the solid arrow 701 in FIG. 7A. When the operation is performed, the volume of the first reservoir between the sealing member 260 and the sealing member 273 increases, and thus the pressure in the first reservoir becomes the negative pressure. However, the priming solution does not flow from the catheter sheath 201 to the first reservoir by the valve 501. Instead, the priming solution in the second reservoir of the syringe 510 flows to the first reservoir having the increased volume via the valve 502. In this manner, the first reservoir having the increased volume is filled with the priming solution.

Figure 7B:
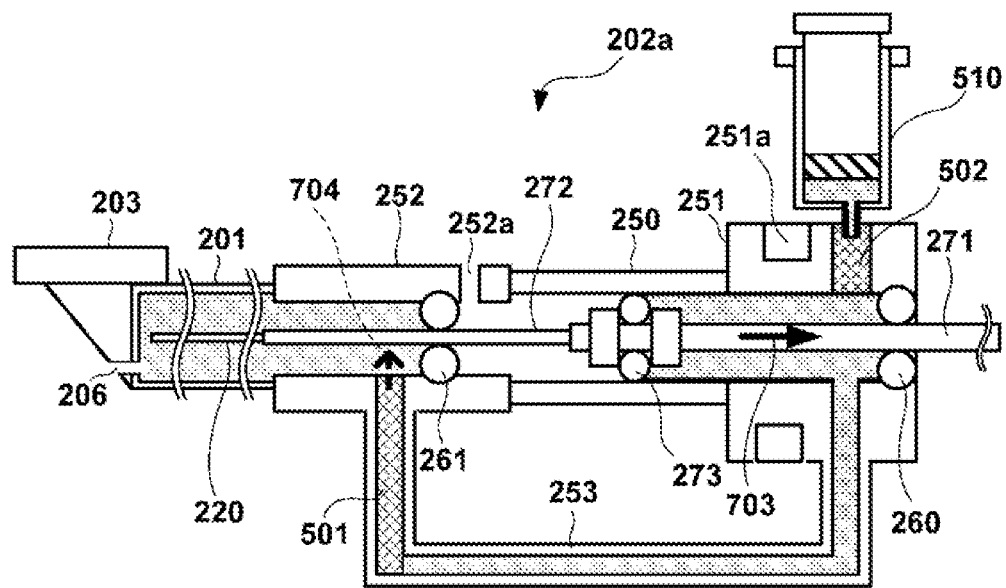

During Pull-back: FIG. 7B

Next, time of the pull-back operation will be described. Although the MDU 102 is omitted in FIG. 7B, similar to the first embodiment described above, the catheter 101 is installed in the MDU 102 when the pull-back is performed.

When the user operates the MDU 102 and inputs the instruction of the pull-back, the MDU 102 starts to move the movable connector and rotates the imaging core 220 in the second connector 202b. As a result, the proximal-side inner tube 271 moves to the right side as shown by a solid arrow 703 in FIG. 7B, and the imaging core 220 in the catheter sheath 201 also moves toward the right side in the figure. When the proximal-side inner tube 271 moves along the solid arrow 703, the volume of the first reservoir defined between the sealing member 260 and the sealing member 273 decreases, and thus the pressure in the first reservoir increases. However, the priming solution does not flow from the first reservoir to the second reservoir by the valve 502. Hence, the priming solution, with which the first reservoir is filled, is pushed to the guide-through route 253 and is supplied to the catheter sheath 201 via the valve 501 as shown by a dashed arrow 704. As a result, a decrease in the internal pressure of the catheter sheath 201 is suppressed. Hence, it is also possible to suppress the flow of blood into the catheter from the priming hole 206 provided at the distal portion of the catheter sheath 201.

Third Embodiment

Figure 8:
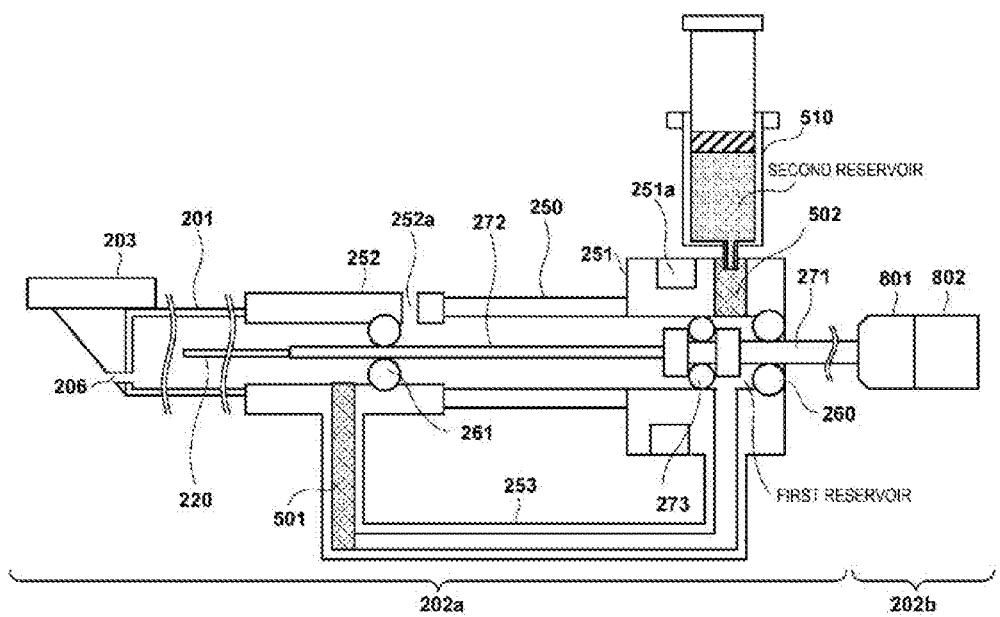
FIG. 8 is a view showing a structure of a catheter in accordance with a third embodiment.

Next, a third embodiment of the present disclosure will be described. FIG. 8 shows a structure of a proximal-side portion (the first connector 202a and the second connector 202b) of the catheter 101 in the third embodiment. The second connector 202b has a connector hub 801 and a joint that is connected to a movable connector of the MDU 102. The third embodiment differs from the second embodiment described above in that the connector hub 801 has a structure in which the priming port 230 is not provided.

The third embodiment is characterized in that the priming of the catheter 101 is performed with the priming solution in the second reservoir of the syringe 510.

The motion of the first connector 202a in the third embodiment is performed without a step in FIG. 6B in the second embodiment by continuously performing the operation of the syringe 510 shown in FIG. 6A until the priming solution is released from the priming hole 206. The subsequent operations are the same as those in FIGS. 7A and 7B.

In the third embodiment, the priming solution is not present in the entire catheter lumen, but only an inside of a sheath in front of the relay connector 252 is filled with the priming solution, and the proximal-side portion (second connector 202b) is not filled with the priming solution.

In addition, pressure is applied to the catheter lumen during the forward during the pull-back; however, the connector hub 801 has a sealing structure, and thus creeping up of the priming solution to the proximal-side (or hand-side portion) can be avoided. In this manner, it is unnecessary to perform the priming by a syringe as known, and thus the priming can be performed through a pull-back/forward motion of the MDU. In addition, it may be necessary or desirable to prepare a dedicated program for the operation control apparatus 103; however, the priming can be manually performed.

As described above, according to the third embodiment, an amount of the priming solution can be reduced, in addition to the effects of the second embodiment. In addition, since the priming is performed without a complicated structure of the proximal-side portion (or hand-side portion), it is possible to suppress forming of air bubbles that bring about air traps of a sensor portion.

OTHER EMBODIMENTS

The first to third embodiments are effective against a backward flow of blood flow due to a pressure difference between the inside and the outside of the catheter. On the other hand, when focusing on a diffusion phenomenon, there is a concern that a blood cell component will infiltrate the inside through the priming hole at the distal end of the catheter even without the pressure difference between the inside and the outside of the catheter. In this manner, a unique structure is provided at the distal portion of the catheter sheath 201, in addition to the first to third embodiments described above. Examples for solving problems arising thereby are described below.

Figure 9A:
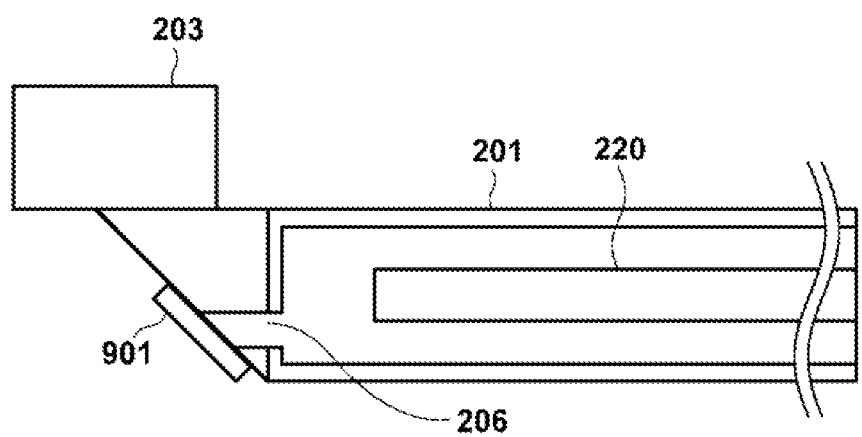
FIGS. 9A, 9B, and 9C are views showing a structural example of a distal portion of a catheter in other exemplary embodiments.

FIG. 9A shows an example in which a valve 901 that opens only in a case where the internal pressure of the catheter sheath 201 is higher than the external pressure of the catheter sheath 201 is provided in the priming hole 206 of the distal portion of the catheter sheath 201. The catheter sheath 201 is filled with the priming solution during the priming operation. In this manner, the internal pressure of the catheter sheath 201 becomes higher than the external pressure of the catheter sheath 201, the valve 901 opens, and the priming solution is discharged. Hence, the user is able to know the completion of the operation of the priming. On the other hand, since the catheter sheath 201 is present in the blood vessel during the pull-back, and the valve 901 remains closed, and thus it is possible to suppress the inflow of the blood.

Figure 9B:
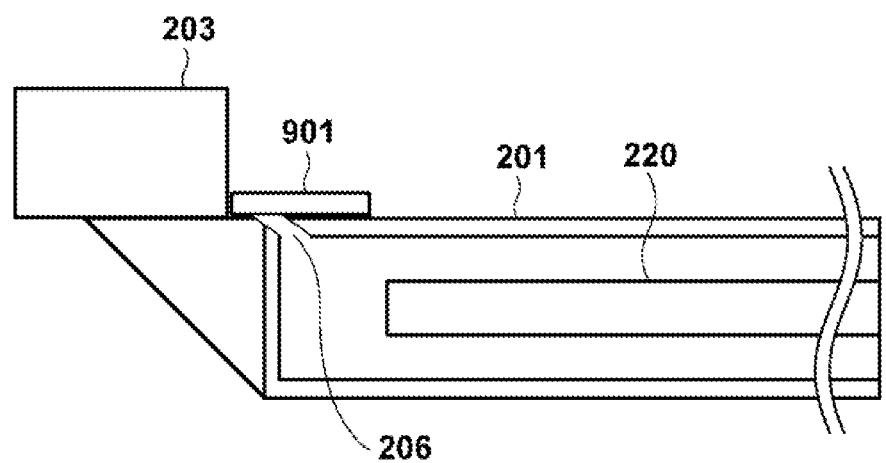

FIG. 9B shows an example in which the priming hole 206 is provided in the vicinity of an opening of the tube 203 for guide wire lumen, through which a guide wire passes, and the valve 901 is provided at a position of the priming hole. In a case where the pull-back operation is actually performed, the guide wire (not shown) penetrates the tube 203 for guide wire lumen. Hence, the guide wire is present immediately on the valve 901 shown in FIG. 9B, it is possible to suppress unintended opening of the valve 901, and thus it is possible to achieve a structure in which reliability more increases compared to the example in FIG. 9A.

Figure 9C:
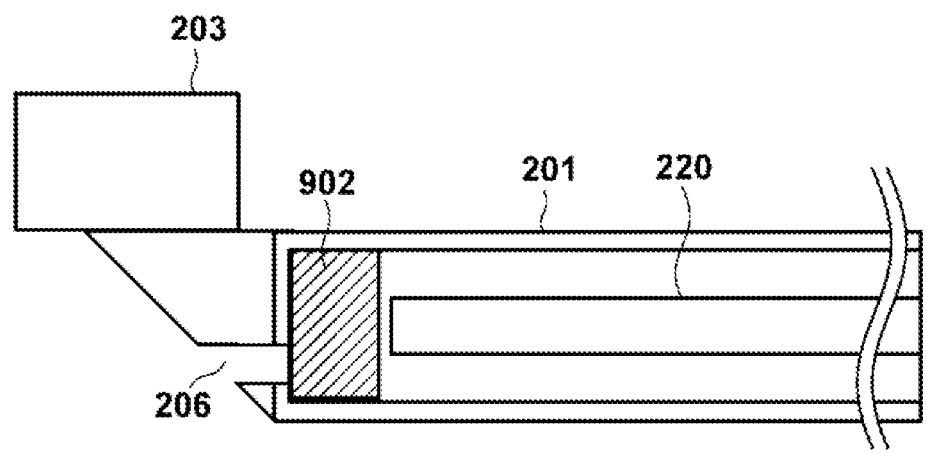

FIG. 9C shows an example in which a filter 902 which has holes, through which it is not possible for erythrocytes to pass, however, air, the priming solution or the like can pass through the filter 902, which is provided at the distal portion of the catheter sheath 201.

The detailed description above describes a catheter for image diagnosis and an imaging apparatus for diagnosis using the catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter for an image diagnosis, the catheter comprising:
    a first connector configured to be supported by a fixed connector portion of a motor drive unit included in an imaging apparatus for diagnosis, the first connector including a structure movably accommodating a support tube and an inner tube, the support tube configured to accommodate an imaging core extending from a second connector, the inner tube configured to accommodate the support tube, and the inner tube is shorter than the support tube, and wherein the first connector further includes a first sealing member configured to seal the support tube and has a fixed position, a second sealing member configured to seal the inner tube and has a fixed position, and a third sealing member configured to be movable together with the inner tube;
    the second connector configured to be supported by a movable connector portion of the motor drive unit, the first and second connectors being located at a proximal portion of the catheter;
    a reservoir in the first connector, the reservoir having a volume which decreases depending on a pull-out length of the second connector from the first connector;
    a supply route configured to supply a priming solution injected from a priming injection port to the reservoir, and wherein the supply route is connected to a priming hole on a distal portion of the catheter;
    an air hole located between the third sealing member and the first sealing member when the inner tube is pushed to a maximum extent; and
    a guide-through route configured to achieve a connection state between the air hole and a space closer to a distal end of the catheter than the first sealing member in a state in which the inner tube is pulled out to the maximum extent and configured to achieve a connection state between the space closer to the distal end of the catheter and a space interposed between the second sealing member and the third sealing member in a case where the inner tube is pushed by at least a preset length, and wherein the reservoir is a space between the second sealing member and the third sealing member.

2. The catheter according to claim 1, wherein
    the priming injection port is located in the second connector; and
    the priming solution injected from the priming injection port flows to a side of the first connector through a gap between the imaging core and the support tube.

3. The catheter according to claim 1, wherein the priming hole includes a valve configured to open when an internal pressure of the catheter is greater than an external pressure of the catheter.

4. The catheter according to claim 3, wherein the valve is located in an opening of a lumen configured for a guide wire and through which the guide wire passes, the lumen being located at the distal end of the catheter.

5. The catheter according to claim 1, wherein the distal portion of the catheter includes a filter configured to prevent erythrocytes from passing and configured to allow the priming solution and air to pass through the filter.

6. An imaging apparatus for diagnosis, comprising:
    a catheter, the catheter comprising:
        a first connector configured to be supported by a fixed connector portion of a motor drive unit, the first connector including a structure movably accommodating a support tube and an inner tube, the support tube configured to accommodate an imaging core extending from a second connector, the inner tube configured to accommodate the support tube, and the inner tube is shorter than the support tube, and wherein the first connector further includes a first sealing member configured to seal the support tube and has a fixed position, a second sealing member configured to seal the inner tube and has a fixed position, and a third sealing member configured to be movable together with the inner tube;
        the second connector configured to be supported by a movable connector portion of the motor drive unit, the first and second connectors being located at a proximal portion of the catheter;
        a reservoir in the first connector, the reservoir having a volume which decreases depending on a pull-out length of the second connector from the first connector;
        a supply route configured to supply a priming solution injected from a priming injection port to the reservoir, and wherein the supply route is connected to a priming hole on a distal portion of the catheter;
        an air hole located between the third sealing member and the first sealing member when the inner tube is pushed to a maximum extent; and
        a guide-through route configured to achieve a connection state between the air hole and a space closer to a distal end of the catheter than the first sealing member in a state in which the inner tube is pulled out to the maximum extent and configured to achieve a connection state between the space closer to the distal end of the catheter and a space interposed between the second sealing member and the third sealing member in a case where the inner tube is pushed by at least a preset length, and wherein the reservoir is a space between the second sealing member and the third sealing member;
        the imaging core configured to be movable and rotatable within the catheter;
        the motor drive unit that rotates the imaging core of the catheter and has a first support for supporting the first connector and a second support for supporting the second connector; and
    means for generating a vascular cross-sectional image by the catheter based on a signal obtained by the catheter via the motor drive unit.

7. The imaging apparatus for diagnosis according to claim 3, wherein
    the priming injection port is located in the second connector; and
    the priming solution injected from the priming injection port flows to a side of the first connector through a gap between the imaging core and the support tube.

8. The imaging apparatus for diagnosis according to claim 6, wherein the priming hole includes a valve configured to open when an internal pressure of the catheter is greater than an external pressure of the catheter, and the valve is located in an opening of a lumen configured for a guide wire and through which the guide wire passes, the lumen being located at the distal end of the catheter.

9. A method of imaging a body lumen inside of a living body, the method comprising:

inserting a catheter into the living body, the catheter including a first connector configured to be supported by a fixed connector portion of a motor drive unit included in an imaging apparatus for diagnosis, the first connector including a structure movably accommodating a support tube and an inner tube, the support tube accommodating an imaging core extending from a second connector, the inner tube configured to accommodate the support tube, and the inner tube is shorter than the support tube, and wherein the first connector further includes a first sealing member configured to seal the support tube and has a fixed position, a second sealing member configured to seal the inner tube and has a fixed position, and a third sealing member configured to be movable together with the inner tube, the second connector configured to be supported by a movable connector portion of the motor drive unit, the first and second connectors being located at a proximal portion of the catheter, a reservoir in the first connector, the reservoir having a volume which decreases depending on a pull-out length of the second connector from the first connector, and a supply route configured to supply a priming solution injected from a priming injection port to the reservoir, and wherein the supply route is connected to a priming hole on a distal portion of the catheter, an air hole located between the third sealing member and the first sealing member when the inner tube is pushed to a maximum extent, and a guide-through route configured to achieve a connection state between the air hole and a space closer to a distal end of the catheter than the first sealing member in a state in which the inner tube is pulled out to the maximum extent and configured to achieve a connection state between the space closer to the distal end of the catheter and a space interposed between the second sealing member and the third sealing member in a case where the inner tube is pushed by at least a preset length, and wherein the reservoir is a space between the second sealing member and the third sealing member;

priming the catheter and the reservoir with the priming solution;

generating a vascular cross-sectional image from a signal obtained by the imaging core of the catheter; and executing a pull-back operation of the catheter along a rotational axis of the catheter which the imaging core is rotating and supplying the priming solution of the reservoir to the distal portion of the catheter via the supply route.

10. The method according to claim 9, wherein the priming of the catheter comprises:

passing the priming solution through the inside of the catheter and discharging the priming solution from the priming hole at the distal end of the catheter; and passing the priming solution through the supply route and flowing the priming solution into the space between the first sealing member and the second sealing member, and discharging the priming solution from the air hole.

* * * * *